United States Patent
Marciacq et al.

(10) Patent No.: US 7,906,666 B2
(45) Date of Patent: Mar. 15, 2011

(54) DHA ENRICHMENT PROCESS

(75) Inventors: Florence Marciacq, Brens (FR);
Mathieu Soulayres, Montreal (CA);
Bernard Freiss, Castres (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 83 days.

(21) Appl. No.: 12/086,771

(22) PCT Filed: Dec. 19, 2006

(86) PCT No.: PCT/EP2006/069899
§ 371 (c)(1), (2), (4) Date: Aug. 15, 2008

(87) PCT Pub. No.: WO2007/071670
PCT Pub. Date: Jun. 28, 2007

(65) Prior Publication Data
US 2009/0036532 A1    Feb. 5, 2009

(30) Foreign Application Priority Data
Dec. 20, 2005    (FR) .................................. 05 12933

(51) Int. Cl.
*C11B 3/00*    (2006.01)
(52) U.S. Cl. ......... 554/205; 554/191; 554/193; 514/560
(58) Field of Classification Search .................. 554/191, 554/193, 205; 514/560
See application file for complete search history.

(56) References Cited

U.S. PATENT DOCUMENTS

| 5,719,302 A * | 2/1998 | Perrut et al. ................... 554/191 |
| 2006/0247455 A1 | 11/2006 | Krumbholz et al. |

FOREIGN PATENT DOCUMENTS

| EP | 0 379 963 A1 | 8/1990 |
| EP | 0 712 651 A1 | 5/1996 |
| EP | 1 419 780 A1 | 5/2004 |
| JP | 2005-255971 A | 9/2005 |

(Continued)

OTHER PUBLICATIONS

Chantachum, S. et al., Separation and quality of fish oil form precooked and non-precooked tuna heads, 2000, Food Chemistry, vol. 69, pp. 289-294.*

(Continued)

*Primary Examiner* — Porfirio Nazario Gonzalez
*Assistant Examiner* — Yate K Cutliff
(74) *Attorney, Agent, or Firm* — Birch, Stewart, Kolasch & Birch, LLP

(57) ABSTRACT

The present invention relates to a continuous process of DHA enrichment of a solution of fatty acids or derivatives thereof comprising less than 50% of DHA relative to the total fatty acids of the solution or to derivatives thereof, wherein the process comprises the steps of (a) simultaneous countercurrent injection, into a fractionation column, of the flow of the solution of fatty acids or of derivatives thereof and of a flow of supercritical $CO_2$ at a temperature of less than or equal to 70° C. and at a pressure of between $100 \times 10^5$ Pa and $160 \times 10^5$ Pa, wherein the level of supercritical $CO_2$ is between 30 and 70, and (b) recovery of the residue comprising at least 50% of DHA relative to the total fatty acids of the residue or to derivatives thereof, wherein the DHA yield is greater than or equal to 60%.

11 Claims, 2 Drawing Sheets

FOREIGN PATENT DOCUMENTS

WO    WO-2004/028470 A2    4/2004

OTHER PUBLICATIONS

Agency for Health Care Research and Quality, Effects of Omega-3 Fatty aicds on cardiovascular disease, Summary, 2004, US Dept. Health and Human Services, No. 94.*

Autoimmune Disease, Medline Plus, Feb. 25, 2010, US Natinal Library of Medicin and NIH, (5 pages).*

Degenerative Nerve Disease, Medline Plus, Feb. 8, 2010, US National Library of Medicine and NIH, (5 pages).*

Kahn, S, Cardiovascular diseases list, Nov. 12, 2009, Buzzle.com, (6 pages).*

Punchard, N. et al., Editorial, 2004, The Journal of Inflammation, BioMed Central, (4 pages).*

Scarpini, E. et al., Treatment of Alzheimer's Disease: current status and new perspectives, 2003, The Lancet Neurology, vol. 2, pp. 539-547.*

Simopoulos, A., Omega-3 Fatty Acids in Inflammation and Autoimmune Diseases, 2002, Journal of the American College of Nutrition, vol. 21, No. 6, pp. 495-505.*

Steenhuysen, J., Omega-3 no match for Alzheimer's study finds, Jul. 21, 2009, Thomson Reuters, (1 page).*

Nilsson et al., JAOCS, Jan. 1988, vol. 65, No. 1, pp. 109-117.

Zhu et al., Proceedings of the 3rd International Symposium on supercritical fluids- Strasbourg, 1994, pp. 95-99.

Fleck et al., Journal of Supercritical Fluids, vol. 14, No. 1, Oct. 1998, pp. 67-74.

Lucien et al., Australasian Biotechnology, vol. 3, No. 3, Jun. 1993, XP008066718, pp. 143-147.

Mishra et al., Food Research International, vol. 26, No. 3, 1993, XP008066737, pp. 217-226.

Riha et al., The Journal of Supercritical Fluids, vol. 17, No. 1, Feb. 2000, pp. 55-64.

Stout et al., Fractionary of fish oils and their fatty acids, Ed. M. E. Stanby, Van Nostrand Reinhold, New-York, 1990, pp. 73-75 and pp. 88-101.

* cited by examiner

DHA ENRICHMENT PROCESS

The present invention relates to a process making it possible, industrially, to enrich a solution of natural fatty acid ethyl esters (fish oil) with a specific fatty acid:docosahexaenoic acid (commonly known as DHA).

BACKGROUND OF THE INVENTION

Oils of marine origin are naturally rich sources of polyunsaturated fatty acids. The most beneficial polyunsaturated fatty acids particularly have the following formulas:

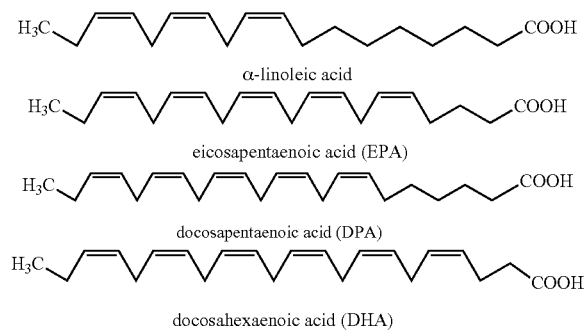

These fatty acids, although they are necessary for the body to function correctly, are not synthesised naturally by the human body. Therefore, the intake thereof is associated with a daily intake via diet. Dietary sources of polyunsaturated fatty acids are vegetable oils (essentially ω-6 and ω-9 type fatty acids) and fish oils which particularly contain large quantities of ω-3 type fatty acids. The latter are very well known for their beneficial effects on health (cardiovascular diseases, auto-immune diseases, inflammations, etc.). Polyunsaturated fatty acids are classified according to the position of the first double bond, from the terminal methyl function. In this way, in the nomenclature ω-x or n-x, the x corresponds to the position of said first unsaturation. The majority of polyunsaturated fatty acids of biological interest belong to the ω-6 (arachidonic acid) or ω-3 (EPA, DHA) family. In addition, in the nomenclature, the number of carbons forming the chain is also defined; in this way, EPA is described as C20:5 and DHA as C22:6. The numbers 5 and 6 correspond to the number of carbon chain unsaturations displayed by EPA and DHA, respectively. Fish oils are essentially used to isolate and concentrate ω-3 type fatty acids.

Conventional fish oil enrichment methods (article by V. K. Mishra et al., Food Research International, 1993, 26, 217-226) are based on selectivity with respect to the length of the fatty acid chains forming the oils or their degree of unsaturation. The most commonly used enrichment processes are performed on fatty acids or the corresponding esters by means of:

Crystallisation
Countercurrent extraction
Molecular distillation
Absorption chromatography.

Most of the time, different processes are combined with a view to obtaining a high level of enrichment. In addition, these processes involve the following drawbacks:

Processes performed at high temperatures (distillation) give rise to multiple thermal degradation products of fatty acids (isomerisation, peroxidation, oligomerisation). For this reason, it is recommended to work at low temperatures, advantageously at temperatures below 100° C.

The drawback of chromatography techniques is based on the use of massive quantities of solvents, which are frequently toxic. In addition, large-scale production based on such techniques is far from easy.

For these reasons, alternative methods have been developed. They are based on the use of supercritical fluids:

Supercritical CO2 fractionating process
Supercritical chromatography.

The fractionating process of fatty acid ethyl esters by means of supercritical $CO_2$ has already been described extensively in the literature. However, it should be noted that the majority of the processes cited describe ω-3 or eicosapentaenoic acid (EPA), and not DHA, enrichment.

One of the operating parameters of the supercritical $CO_2$ fractionating process is the level of supercritical $CO_2$. This level is defined by the ratio of the $CO_2$ flow over the flow of injected fatty acid solution. In this way, at high levels of supercritical $CO_2$, the selectivity is increased to the detriment of the yield. At low levels of supercritical $CO_2$, the yield is favoured while the selectivity is decreased.

In this way, Nilsson et al. (JAOCS 1988, 65 (1), 109-117) describe a batch process making it possible to obtain several fractions (0.1 to 0.2 g) rich in EPA and DHA respectively. For this purpose, the authors worked at pressures between $220*10^5$ Pa and $250*10^5$ Pa. In addition, they produced a temperature gradient in the column to generate an internal reflux (from 20° C. at column bottom to 100° C. at column head). The levels of supercritical $CO_2$ defined are very high, of the order of 100 to 500.

Some tests make it possible to obtain, from ethyl esters pre-treated with urea, fractions having a DHA content of the order of 90%, but with levels of supercritical $CO_2$ of 500.

Using non-treated ethyl esters, the authors described DHA-rich fractions (content between 53 and 60%) but for levels of supercritical $CO_2$ of the order of 300 to 400.

Therefore, this process has the following drawbacks: it consists of a batch process. The level of supercritical $CO_2$ used is too high and the process must therefore have a low yield, which cannot be used industrially. In fact, this induces additional energy costs and therefore lower productivity. The temperature of 100° C. at the column head may induce fatty acid degradation. However, this is the temperature recommended by the authors. The pressures used are too high and, if they were reduced, there would be an increase in the level of supercritical $CO_2$. Moreover, this article recommends the use of a temperature gradient within the column and, in particular, an internal reflux in order to improve separation and therefore enrichment. However, the presence of such a reflux decreases the productivity of the process.

Kado et al. (JP2005-255971) describe in their patent a fish oil ethyl ester enrichment process with EPA and DHA. The temperature and pressure ranges claimed are 35-200° C. and $100*10^5$ Pa-$500*10^5$ Pa. The authors recommend two successive extractions in order to obtain high contents. A first extraction is performed on the raw material, and a second extraction is performed on the residue from the first operation. The column used is 3 m high for an inner diameter of 50 mm. It comprises 6 separate heating chambers. The two successive extractions complicate the process and render it industrially inapplicable.

The levels of supercritical $CO_2$ used to obtain high DHA contents are high (of the order of 127). Therefore, the DHA yield is low. Moreover, the authors recommend the application of a temperature gradient (which makes it possible to obtain a rectification effect) in the column. Therefore, the productivity is restricted.

Lucien et al. (Australasian biotechnology, 1993, 3 (3), 143-147) describe a process to obtain EPA and DHA ethyl ester-enriched extracts from 17/12 (EPA/DHA) sardine oil. An internal reflux generated by a heating chamber placed at the column head makes it possible to improve the contents obtained: EPA and DHA contents of 42% and 54%, respectively, may be achieved. The best operating conditions in this configuration are $150*10^5$ Pa, 40° C. in the column and a reflux temperature of 100° C. The level of supercritical $CO_2$ used is not specified.

The table below contains the results obtained:

| Pressure (Pa) | Extraction temperature (° C.) | Reflux temperature (° C.) | [EPA] (%) | [DHA] (%) |
| --- | --- | --- | --- | --- |
| $150 * 10^5$ | 40 | 60 | 21 | 34 |
| $150 * 10^5$ | 40 | 80 | 33 | 39 |
| $150 * 10^5$ | 40 | 100 | 42 | 54 |

Therefore, this process has the following drawbacks: the temperature of 100° C. in the column head may induce fatty acid degradation. However, this is the temperature recommended by the authors. Moreover, this article recommends the use of a temperature gradient within the column and, in particular, an internal reflux in order to improve separation and therefore enrichment. However, the presence of such a reflux decreases the productivity of the process.

Finally, Zhu et al. (Proceedings of the $3^{rd}$ International Symposium on supercritical fluids—Strasbourg, 1994) describe a fatty acid ethyl ester extraction/fractionating process in order to obtain fractions rich in EPA and DHA, respectively. For this purpose, a $CO_2$ flow extracts the fatty acid esters contained in an extractor, and this $CO_2$ flow charged with esters is then fractionated in a column. A temperature gradient and pressure programming are performed in the column, in order to improve the selectivity with respect to the compounds under test. This batch process makes it possible to isolate a fraction representing 12% of the DHA used with more than 50% purity.

Therefore, this process has the following drawbacks: it consists of a batch process and, for this reason, it may comprise pressure programming. The level of supercritical $CO_2$ used is very high (211) and the process must therefore have a low yield, which is not industrially usable. In fact, this induces additional energy costs and therefore lower productivity. Moreover, this article recommends the use of a temperature gradient within the column and, in particular, an internal reflux in order to improve separation and therefore enrichment. However, the presence of such a reflux decreases the productivity of the process.

Therefore, the majority of the processes described in the literature use a high level of supercritical $CO_2$, which gives a very low DHA yield and therefore a process which is not industrially feasible. In addition, for a process to be industrially feasible, it is also necessary not to work at an excessively high pressure. However, when the pressure decreases, the density decreases and it is therefore necessary to increase the level of supercritical $CO_2$ to obtain an equivalent DHA content. Therefore, it is necessary to find a compromise between the pressure, level of supercritical $CO_2$ and yield, in order to obtain a beneficial DHA enrichment, i.e. at least 50%. Moreover, only continuous processes are of interest from an industrial point of view.

Finally, in order to prevent the degradation of fatty acids and of DHA in particular, it is advisable to work at a low temperature, i.e. a temperature less than 100° C. and in particular less than or equal to 70° C.

In addition, it is also advisable to find a process making it possible to enrich a fatty acid solution with DHA only using a single countercurrent fractionating step, not requiring pre-treatment of the fatty acids with urea.

SUMMARY OF THE INVENTION

In this way, the inventors discovered surprisingly that a temperature of not more than 70° C., a pressure between $100*10^5$ Pa and $160*10^5$ Pa and a level of supercritical $CO_2$ between 30 and 70 made it possible, as part of a single supercritical $CO_2$ countercurrent fractionating step, to obtain at least 50% DHA enrichment, from a solution of fatty acids or of derivatives thereof comprising less than 50% DHA relative to the total fatty acids of the solution or the derivatives thereof, not having being pre-treated with urea.

Therefore, the present invention relates to a continuous process of DHA enrichment of a solution of fatty acids or of derivatives thereof comprising less than 50% DHA relative to the total fatty acids of the solution or to the derivatives thereof, wherein the process comprises the steps of (a) simultaneous countercurrent injection, into a fractionating column of the flow of the solution of fatty acids or of derivatives thereof and of a flow of supercritical $CO_2$ at a temperature of less than or equal to 70° C. and at a pressure between $100*10^5$ Pa and $160*10^5$ Pa, advantageously between $120*10^5$ Pa and $140*10^5$ Pa, wherein the level of supercritical $CO_2$ is between 30 and 70, advantageously between 30 and 40, and (b) recovery of the residue comprising at least 50% DHA relative to the total fatty acids of the residue or to derivatives thereof, wherein the DHA yield is greater than or equal to 60%.

Unless specified otherwise, the DHA (or EPA) percentages relative to the total fatty acids or to the derivatives thereof are expressed as area percentages. In fact, these values correspond to the peak area attributed to DHA (or EPA) divided by the sum of all the peak areas attributed to fatty acids present in the solution or residue. These peaks are obtained by means of gas chromatography according to the method described in the experimental part and the area thereof is measured on the chromatograms obtained.

According to the present invention, the term "fatty acid derivatives" refers to fatty acid esters, particularly methyl or ethyl esters. Advantageously, it refers to ethyl esters.

Advantageously, the solution of fatty acids or of derivatives thereof used is an unprocessed solution, i.e. not undergoing pre-treatment with urea, the fatty acids and derivatives thereof therefore not being complexed with urea. Advantageously, it consists of an ethyl ester solution.

Advantageously, the solution of fatty acids or of derivatives thereof used comprises at least 20%, advantageously at least 25% DHA relative to the total fatty acids of the solution or to derivatives thereof.

In a specific embodiment of the invention, the solution of fatty acids or of derivatives thereof is a fish or seaweed oil, advantageously a fish oil. In particular, it consists of a tuna or cod liver oil.

In particular, this oil comprises at least 20%, advantageously at least 25% DHA relative to the total fatty acids of the oil or to the derivatives thereof. In particular, the cod liver oil has the following composition, with respect to the main fatty acids thereof:

| Fatty acid | Cod liver oil (%) |
| --- | --- |
| 14:0 | 1.1 |
| 16:0 | 18.5 |
| 16:1 | 3.7 |
| 18:0 | 5.3 |
| 18:1 | 14.7 |
| 18:2 ω 6 | 1.7 |
| 20:1 | 9.8 |
| 20:4 ω 6 | 0.4 |
| 20:5 ω 3 (EPA) | 6.4 |
| 22:1 | 2.3 |
| 22:6 ω 3 (DHA) | 27.4 |
| Total saturated | 29.1 |
| Total monounsaturated | 29.7 |
| Total ω 6 (LA + AA) | 2.1 |
| Total ω 3 (EPA + DHA) | 33.8 |

Advantageously, the tuna oil used comprises 55% EPA and 26.6% DHA. Advantageously, the chromatogram thereof obtained by means of gas chromatography using the method described hereinafter in the examples is represented in FIG. 1.

Advantageously, it consists of 25 DHA tuna oil marketed by POLARIS or PRONOVA BIOCARE.

According to the present invention, the term "level of supercritical $CO_2$" refers to the ratio of the flow rate of supercritical $CO_2$ over the flow rate of solution of fatty acids or of derivatives thereof.

Therefore, the process according to the present invention consists of simultaneous countercurrent injection, into a fractionating column, of the solution of fatty acids or of derivatives thereof and supercritical $CO_2$. The latter is injected at the column bottom, while the solution of fatty acids or of derivatives thereof is injected higher into the column. The flow of $CO_2$ is progressively charged with the more volatile compounds extracted. These compounds are recovered after depressurisation in cyclone separators.

In a specific embodiment of the invention, the temperature at the column bottom is less than the temperature at the column head. Therefore, there is a temperature gradient within the column. Advantageously, the temperature at the column head is between 55 and 70° C. and the temperature at the column bottom is between 35 and 50° C.

The presence of this gradient decreases the productivity of the process but increases the DHA yield. In fact, the temperature gradient induces an internal reflux which may cause clogging of the column. Therefore, it is necessary to work with lower solution flow rates.

In another embodiment of the invention, the temperature of step (a) is constant in the column. Therefore, there is no temperature gradient. Advantageously, the temperature is between 40 and 70° C. The absence of this gradient improves productivity but decreases the DHA yield.

In an advantageous embodiment, the fractionating column is at least 1.5 m long and has an inner diameter of at least 20 mm, advantageously at least 8 m long and having an internal diameter of at least 126 mm.

In another embodiment, the pressure used in the column is $135*10^5$ Pa.

Therefore, the process according to the present invention makes it possible to obtain a residue comprising at least 50% DHA relative to the total fatty acids of the residue or to the derivatives thereof, advantageously between 50 and 70% DHA. This residue is extracted continuously at the column bottom. Advantageously, this residue comprises at least 52% DHA, advantageously at least 55% DHA, and more advantageously at least 60% DHA relative to the total fatty acids of the residue or to derivatives thereof.

Advantageously, the DHA yield of the process according to the invention is at least 60%, advantageously at least 65%, and more advantageously at least 70%. In the case of a temperature gradient in the column, this yield is advantageously at least 80%.

The present invention also relates to a solution of fatty acids or of derivatives thereof containing at least 50% DHA obtainable by means of the process according to the present invention.

It also relates to a solution of fatty acids or of derivatives thereof according to the present invention for use thereof as a medicinal product.

Finally, it relates to a solution of fatty acids or of derivatives thereof according to the present invention for use thereof as a medicinal product intended to treat neurodegenerative diseases, such as Alzheimer's disease, cardiovascular diseases, auto-immune diseases and/or inflammations.

BRIEF DESCRIPTION OF THE DRAWINGS

The invention will be understood more clearly in view of the figures and examples hereinafter.

DETAILED DESCRIPTION OF THE INVENTION

The analysis protocol of the enriched solutions and the initial tuna oil is as follows:

The composition of the enriched solutions and the initial tuna oil is performed by means of gas chromatography, according to the following method:

Apparatus: Gas Chromatography with flame ionisation detector

Operating Conditions:

| | | |
| --- | --- | --- |
| Column | Type: | CP-WAX 52CB |
| | Length (m): | 25 |
| | Diameter (mm): | 0.25 |
| | | 0.20 |
| Gas | Carrier gas: | Helium |
| | Column head pressure: | $1.38 * 10^5$ Pa |
| | Pressure mode or constant flow rate: | constant flow rate |
| | Column flow rate (ml/min): | 1.4 |
| Injector | Temperature (° C.): | 250 |
| | Leakage rate (split) (ml/min): | 280 |
| | Liner type (deactivated/not deactivated): | deactivated |
| | Liner volume (μl): | 860 |
| Detector | Temperature (° C.): | 270 |
| | Hydrogen flow rate (ml/min): | 30 |
| | Oxygen flow rate (ml/min): | 300 |
| | Make-up + column (ml/min): | 30 |

| Oven programme | Gradient (° C./min) | Temperature (° C.) | Time (min) |
| --- | --- | --- | --- |
| | | 170 | 2 |
| | 2.95 | 240 | 2.30 |
| Run time (min) | | 28.03 | |
| Injection volume (μl) | | 1 | |

Methodology:

Control Solution Preparation:

In a 5.0 ml flask, introduce 30 mg of docosahexaenoic acid SCR (DHA) ethyl ester, 45 mg of eicosapentaenoic acid SCR (EPA) ethyl ester. Dissolve in a 50 mg/l butylhydroxytoluene solution R in trimethylpentane R and make up to the volume with the same solution.

Test Solution Preparation (2 Tests):

In a 10.0 ml flask, introduce 0.5 g of test substance. Dissolve in a 50 mg/l butylhydroxytoluene solution R in trimethylpentane R and make up to the volume with the same solution.

Processing of Results:

Note the % areas of eicosapentaenoic acid (EPA) ethyl ester and docosahexaenoic acid (DHA) ethyl ester in the test solution.

The following examples are given as a non-limitative indication.

Example 1

Figure 1:
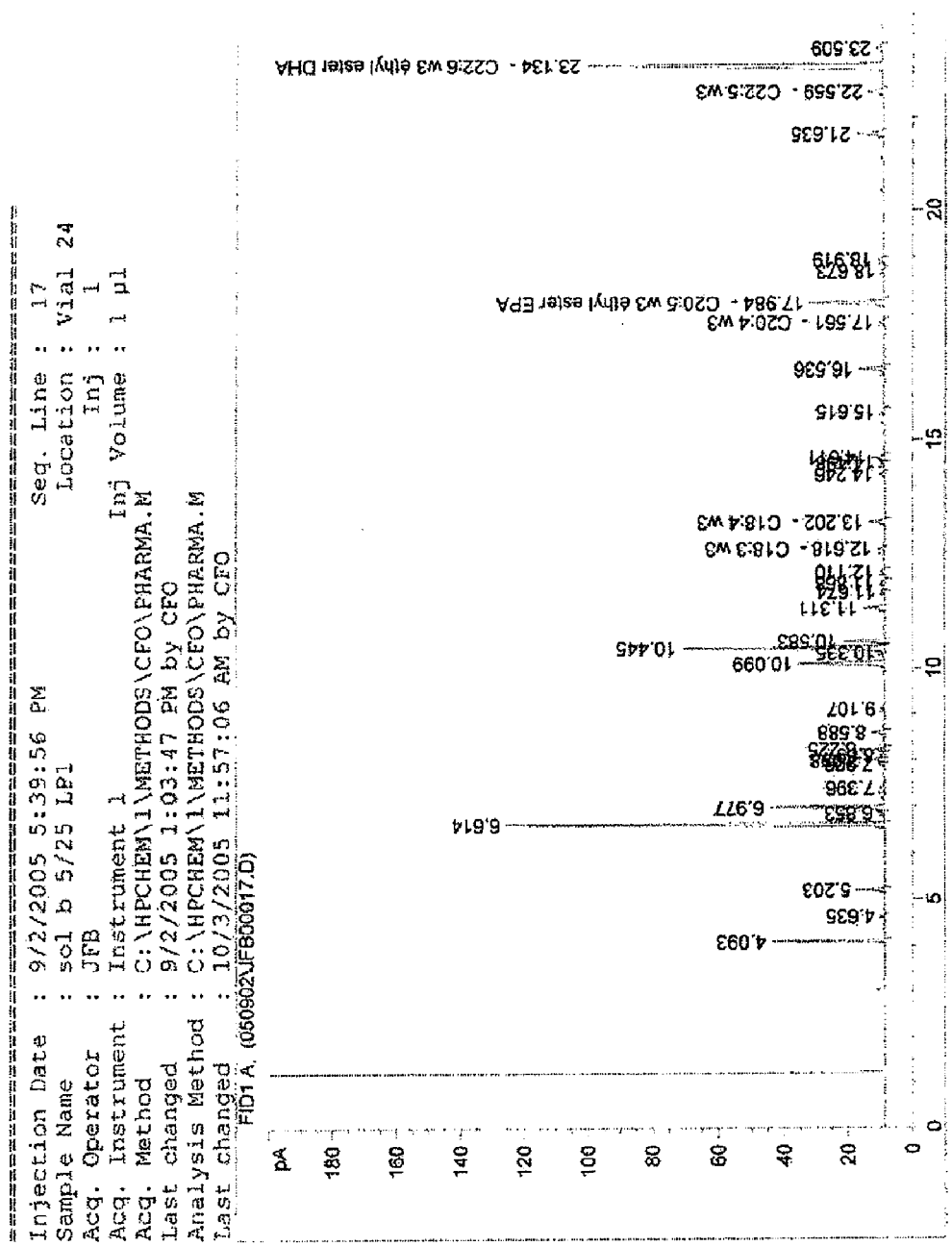
FIG. 1 represents a chromatogram obtained by means of gas chromatography of the tuna oil used in the examples.
Figure 2:
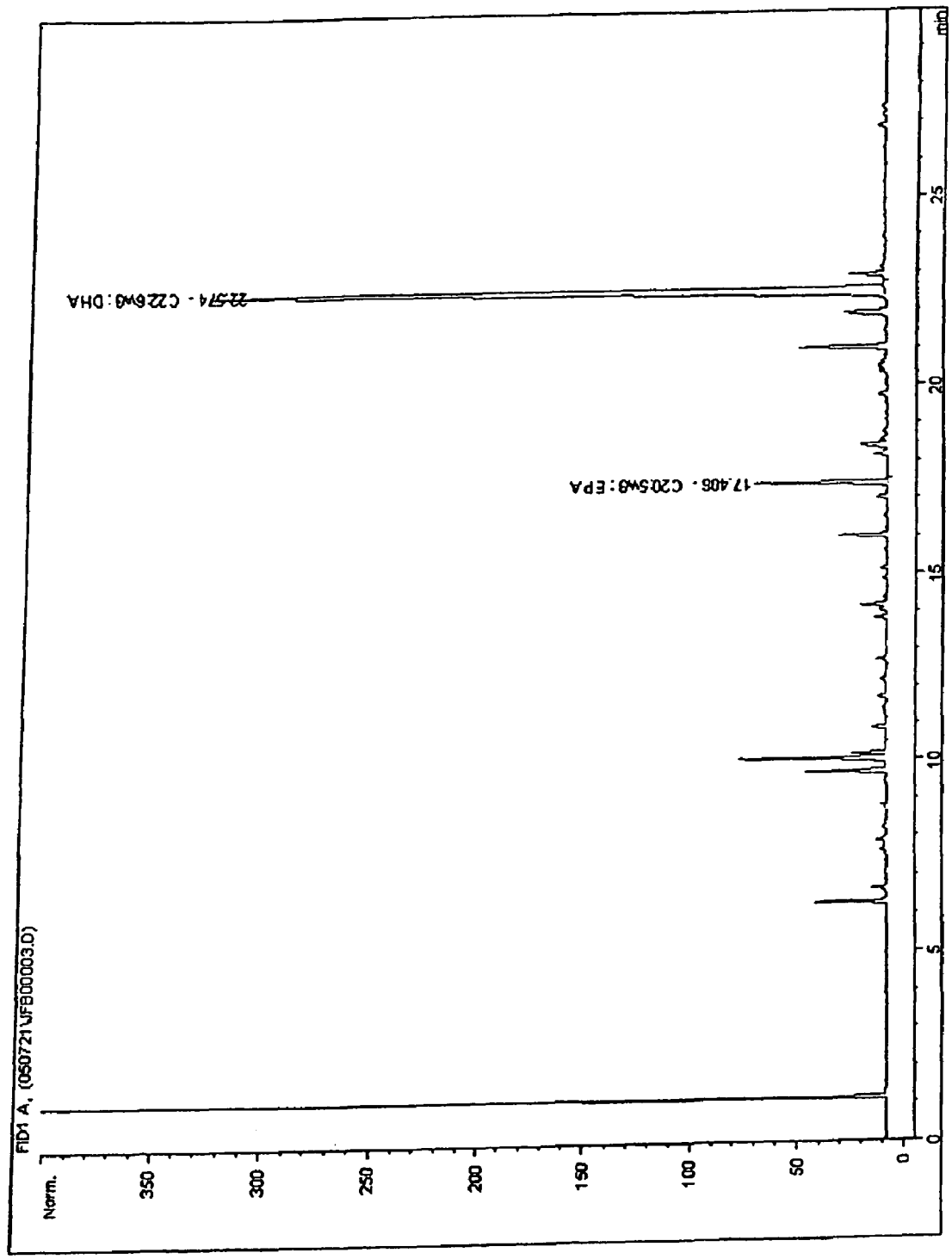
FIG. 2 represents a chromatogram obtained by means of gas chromatography on the enriched residue obtained in example 1.

On a 1.5 m high and 20 mm inner diameter packed laboratory column, 1520 g of 25 DHA tuna oil marketed by POLARIS, the chromatogram whereof is represented in FIG. 1 and containing 5.5% EPA and 26.6% DHA, is injected. The total injection time is 4 hours.

The operating parameters are as follows:
Pressure and temperature in column: $135*10^5$ Pa-60° C.
Solution injection flow rate: 280 g/hr.
$CO_2$ flow rate: 19 kg/hr.
Therefore, the level of supercritical $CO_2$ is 67.8.

The enriched solution is extracted continuously at the column bottom. In this way, 534 g of a solution of fatty acid ethyl esters containing 55.0% DHA relative to the total fatty acids or to derivatives thereof is recovered. The DHA recovery yield is 77%.

Example 2

On a 8 m high and 126 mm inner diameter packed industrial column, 210.6 kg of 25 DHA tuna oil marketed by POLARIS, the chromatogram whereof is represented in FIG. 1 and containing 5.5% EPA and 26.6% DHA, is injected. The total injection time is 9 hours.

The operating parameters are as follows:
Pressure and temperature in column: $135*10^5$ Pa-60° C.
Solution injection flow rate: 23 kg/hr.
$CO_2$ flow rate: 900 kg/hr.
Therefore, the level of supercritical $CO_2$ is 39.1.

The enriched solution is extracted continuously at the column bottom. In this way, 63.3 kg of a solution of fatty acid ethyl esters containing 63.7% DHA relative to the total fatty acids or to derivatives thereof is recovered. The DHA recovery yield is 64%.

Example 3

On a 8 m high and 126 mm inner diameter packed industrial column, 203.0 kg of 25 DHA tuna oil marketed by POLARIS, the chromatogram whereof is represented in FIG. 1 and containing 5.5% EPA and 26.6% DHA, is injected. The total injection time is 8.5 hours.

The operating parameters are as follows:
Pressure and temperature in column: $135*10^5$ Pa-60° C.
Solution injection flow rate: 24 kg/hr.
$CO_2$ flow rate: 800 kg/hr.
Therefore, the level of supercritical $CO_2$ is 33.3.

The enriched solution is extracted continuously at the column bottom. In this way, 85.4 kg of a solution of fatty acid ethyl esters containing 53.5% DHA relative to the total fatty acids or to derivatives thereof is recovered. The DHA recovery yield is 75%.

Example 4

On a 1.5 m high and 20 mm inner diameter packed laboratory column, 333 g of 25 DHA tuna oil marketed by POLARIS, the chromatogram whereof is represented in FIG. 1 and containing 5.5% EPA and 26.6% DHA, is injected. The total injection time is 1 hour 45.

The operating parameters are as follows:
Pressure and temperature in column: $135*10^5$ Pa.
Temperature gradient in column: 45° C. at column bottom and 65° C. at column head.
Solution injection flow rate: 220 g/hr.
$CO_2$ flow rate: 15 kg/hr.
Therefore, the level of supercritical $CO_2$ is 68.

The enriched solution is extracted continuously at the column bottom. In this way, 166 g of a solution of fatty acid ethyl esters containing 50% DHA relative to the total fatty acids or to derivatives thereof is recovered. The DHA recovery yield is 88% and the productivity 95 g/hr.

Example 5

On a 1.5 m high and 20 mm inner diameter packed laboratory column, 800 g of 25 DHA tuna oil marketed by POLARIS, the chromatogram whereof is represented in FIG. 1 and containing 5.5% EPA and 26.6% DHA, is injected. The total injection time is 1 hour 50.

The operating parameters are as follows:
Pressure and temperature in column: $135*10^5$ Pa-60° C.
Solution injection flow rate: 440 g/hr.
$CO_2$ flow rate: 29 kg/hr.
Therefore, the level of supercritical $CO_2$ is 65.9.

The enriched solution is extracted continuously at the column bottom. In this way, 272 g of a solution of fatty acid ethyl esters containing 51.0% DHA relative to the total fatty acids or to derivatives thereof is recovered. The DHA recovery yield is 65%. The productivity is 160 g/hr.

The invention claimed is:

1. Continuous process of DHA enrichment of a solution of fatty acids or of derivatives thereof comprising less than 50% DHA relative to the total fatty acids of the solution or to the derivatives thereof, wherein the process comprises the steps of
   (a) simultaneous countercurrent injection, into a fractionating column of the flow of the solution of fatty acids or of derivatives thereof and of a flow of supercritical $CO_2$ at a temperature of less than or equal to 70° C. and at a pressure between $100 \times 10^5$ Pa and $160 \times 10^5$ Pa, wherein the level of supercritical $CO_2$ is between 30 and 70 and
   (b) recovery of a residue comprising at least 50% DHA relative to the total fatty acids of the residue or to derivatives thereof, wherein the DHA yield is greater than or equal to 60%.

2. The process according to claim 1 wherein the temperature at the column bottom is less than the temperature at the column head.

3. The process according to claim 1 wherein the temperature of step (a) is constant in the column.

4. The process according to claim 1 wherein step (a) is performed at a pressure between $120 \times 10^5$ Pa and $140 \times 10^5$ Pa.

5. The process according to claim 1 wherein the solution of fatty acids or of derivatives thereof is a solution of fish oil.

6. The process according to claim 5 wherein the fish oil solution comprises at least 20% DHA relative to the total fatty acids of the fish oil solution or to derivatives thereof.

7. The process according to claim 1 wherein the solution of fatty acids or of derivatives thereof is a fatty acid ethyl ester solution.

8. The process according to claim 1 wherein the level of supercritical $CO_2$ of step (a) is between 30 and 40.

9. The process according to claim 2 wherein the temperature at the column head is between 55 and 70° C. and the temperature at the column bottom is between 35 and 50° C.

10. The process according to claim 3 wherein the temperature of a step (a) is between 40 and 70° C.

11. The process according to claim 5 wherein the solution of fatty acids or of derivatives thereof is a solution of tuna or cod liver oil.

* * * * *